(12) United States Patent
Jang et al.

(10) Patent No.: US 10,312,542 B2
(45) Date of Patent: Jun. 4, 2019

(54) HALOGENATED COMPOUND, POLYMER COMPRISING SAME, AND POLYMER ELECTROLYTE MEMBRANE COMPRISING SAME

(71) Applicant: LG CHEM, LTD., Seoul (KR)

(72) Inventors: Yong Jin Jang, Daejeon (KR); Joong Jin Han, Daejeon (KR); Sehee Jung, Daejeon (KR); Youngjea Kim, Daejeon (KR); Esder Kang, Daejeon (KR); Hyun Woog Ryu, Daejeon (KR)

(73) Assignee: LG CHEM, LTD., Seoul (KR)

( * ) Notice: Subject to any disclaimer, the term of this patent is extended or adjusted under 35 U.S.C. 154(b) by 139 days.

(21) Appl. No.: 15/531,667

(22) PCT Filed: Dec. 4, 2015

(86) PCT No.: PCT/KR2015/013202
§ 371 (c)(1),
(2) Date: May 30, 2017

(87) PCT Pub. No.: WO2016/089152
PCT Pub. Date: Jun. 9, 2016

(65) Prior Publication Data
US 2017/0338507 A1    Nov. 23, 2017

(30) Foreign Application Priority Data

Dec. 4, 2014   (KR) .......................... 10-2014-0173137
Dec. 4, 2014   (KR) .......................... 10-2014-0173157
(Continued)

(51) Int. Cl.
H01M 8/18        (2006.01)
H01M 8/1039   (2016.01)
(Continued)

(52) U.S. Cl.
CPC ........... *H01M 8/188* (2013.01); *C07C 323/66* (2013.01); *C08F 28/04* (2013.01); *C08G 61/02* (2013.01);
(Continued)

(58) Field of Classification Search
CPC .... H01M 8/18; H01M 8/1023; H01M 8/1032; H01M 8/1039; C08F 28/00; C08F 28/04
See application file for complete search history.

(56) References Cited

U.S. PATENT DOCUMENTS 7,807,759 B2    10/2010    Shin et al.
9,136,551 B2     9/2015    Kwon et al.
(Continued)

FOREIGN PATENT DOCUMENTS

EP    2270104 A1    1/2011
JP    2003-234014 A    8/2003
(Continued)

OTHER PUBLICATIONS

Arvai et al., "New aryl-containing fluorinated sulfonic acids and their ammonium salts, useful as electrolytes for fuel cells or ionic liquids", Journal of Fluorine Chemistry, vol. 129, 2008, pp. 1029-1035.
(Continued)

*Primary Examiner* — Kenneth J Douyette
(74) *Attorney, Agent, or Firm* — Birch, Stewart, Kolasch & Birch, LLP

(57) ABSTRACT

The present specification relates to a halogenated compound, a polymer and a polymer electrolyte membrane including the same.

20 Claims, 3 Drawing Sheets

(30) Foreign Application Priority Data

Dec. 4, 2014 (KR) ........................ 10-2014-0173178
Dec. 1, 2015 (KR) ........................ 10-2015-0170044

(51) Int. Cl.

| | |
|---|---|
| H01M 8/1023 | (2016.01) |
| C08F 28/04 | (2006.01) |
| C08G 81/00 | (2006.01) |
| C08J 5/22 | (2006.01) |
| C08G 61/02 | (2006.01) |
| C08G 75/20 | (2016.01) |
| H01M 8/1032 | (2016.01) |
| C07C 323/66 | (2006.01) |
| C08L 63/00 | (2006.01) |
| H01M 8/1025 | (2016.01) |
| H01M 8/1053 | (2016.01) |

(52) U.S. Cl.

CPC ............. *C08G 75/20* (2013.01); *C08G 81/00* (2013.01); *C08J 5/2262* (2013.01); *C08L 63/00* (2013.01); *H01M 8/1023* (2013.01); *H01M 8/1025* (2013.01); *H01M 8/1032* (2013.01); *H01M 8/1039* (2013.01); *H01M 8/1053* (2013.01); *C08J 2371/10* (2013.01); *H01M 2300/0082* (2013.01); *Y02E 60/528* (2013.01)

(56) References Cited

U.S. PATENT DOCUMENTS

| 9,912,002 | B2 | 3/2018 | Kong |
|---|---|---|---|
| 2004/0048129 | A1 | 3/2004 | Taft, III et al. |
| 2005/0031924 | A1 | 2/2005 | Shirono et al. |
| 2005/0053818 | A1 | 3/2005 | St-Arnaud et al. |
| 2006/0188768 | A1 | 8/2006 | Kanaoka et al. |
| 2008/0114149 | A1 | 5/2008 | Moore et al. |
| 2008/0114183 | A1 | 5/2008 | Moore et al. |
| 2009/0123641 | A1 | 5/2009 | Romdhane et al. |
| 2009/0163692 | A1 | 6/2009 | Moore et al. |
| 2009/0169950 | A1 | 7/2009 | Prugh et al. |
| 2010/0167100 | A1 | 7/2010 | Moore et al. |
| 2011/0020731 | A1 | 1/2011 | Yoshimura et al. |
| 2011/0059385 | A1 | 3/2011 | Kim et al. |
| 2011/0136040 | A1 | 6/2011 | Hwang et al. |
| 2012/0028138 | A1 | 2/2012 | Lee et al. |
| 2012/0052347 | A1 | 3/2012 | Wilson et al. |
| 2012/0135333 | A1 | 5/2012 | Meredith, III et al. |
| 2014/0030573 | A1 | 1/2014 | Esswein et al. |
| 2014/0065512 | A1 | 3/2014 | Kwon et al. |
| 2014/0227627 | A1 | 8/2014 | He et al. |
| 2016/0260994 | A1 | 9/2016 | Kong |
| 2016/0380297 | A1 | 12/2016 | Kong et al. |
| 2017/0338504 | A1 | 11/2017 | Kang et al. |

FOREIGN PATENT DOCUMENTS

| JP | 2004-335231 A | 11/2004 |
|---|---|---|
| JP | 2006-228628 A | 8/2006 |
| JP | 2009-256654 A | 11/2009 |
| JP | 2011-57982 A | 3/2011 |
| JP | 2012-149259 A | 8/2012 |
| JP | 2013-218868 A | 10/2013 |
| KR | 10-2003-0076057 A | 9/2003 |
| KR | 10-2006-0071690 A | 6/2006 |
| KR | 10-2006-0100148 A | 9/2006 |
| KR | 10-2010-0076902 A | 7/2010 |
| KR | 10-2010-0084237 A | 7/2010 |
| KR | 10-2011-0063175 A | 6/2011 |
| KR | 10-2013-0062252 A | 6/2013 |
| KR | 10-2015-0048639 A | 5/2015 |
| WO | WO 2006/132144 A1 | 12/2006 |

OTHER PUBLICATIONS

International Search Report issued in PCT/KR2015/013202 (PCT/ISA/210), dated Apr. 6, 2016.
International Search Report issued in PCT/KR2015/013203 (PCT/ISA/210), dated Apr. 6, 2016.
International Search Report issued in PCT/KR2015/013206 (PCT/ISA/210), dated Apr. 7, 2016.
International Search Report issued in PCT/KR2015/013209 (PCT/ISA/210), dated Apr. 1, 2016.
International Search Report issued in PCT/KR2015/013213 (PCT/ISA/210), dated May 19, 2016.
International Search Report issued in PCT/KR2015/013218 (PCT/ISA/210), dated Apr. 8, 2016.
Paillard et al., "Electrochemical investigation of polymer electrolytes based on lithium 2-(phenylsulfanyl)-1,1,2,2-tetrafluoroethansulfonate", Electrochimica Acta, vol. 53, 2007, pp. 1439-1443.
Paillard et al., "Polymer electrolytes based on new aryl-containing lithium perfluorosulfonates", Journal of Fluorine Chemistry, vol. 134, 2012, pp. 72-76.
Toulgoat et al., "An Efficient Preparation of New Sulfonyl Fluorides and Lithium Sulfonates", The Journal of Organic Chemistry, vol. 72, No. 24, 2007, pp. 9046-9052.
Xu et al., "Highly Conductive Aromatic Ionomers with Perfluorosulfonic Acid Side Chains for Elevated Temperature Fuel Cells", Macromolecules, vol. 44, 2011, pp. 4605-4609.
European Search Report for Appl. No. 15865952.4 dated May 29, 2018.
U.S. Office Action for U.S. Appl. No. 15/531,702, dated Sep. 7, 2018.
Extended European Search Report dated Mar. 28, 2018 for Application No. 15865281.8.
Extended European Search Report dated Mar. 28, 2018 for Application No. 15866009.2.
Extended European Search Report dated Mar. 28, 2018 for Application No. 15866198.3.
U.S. Office Action for U.S. Appl. No. 15/531,584, dated Dec. 13, 2018.
U.S. Office Action for U.S. Appl. No. 15/531,670, dated Feb. 1, 2019.
U.S. Office Action for U.S. Appl. No. 15/531,596 dated Apr. 12, 2019.

[FIG. 1]
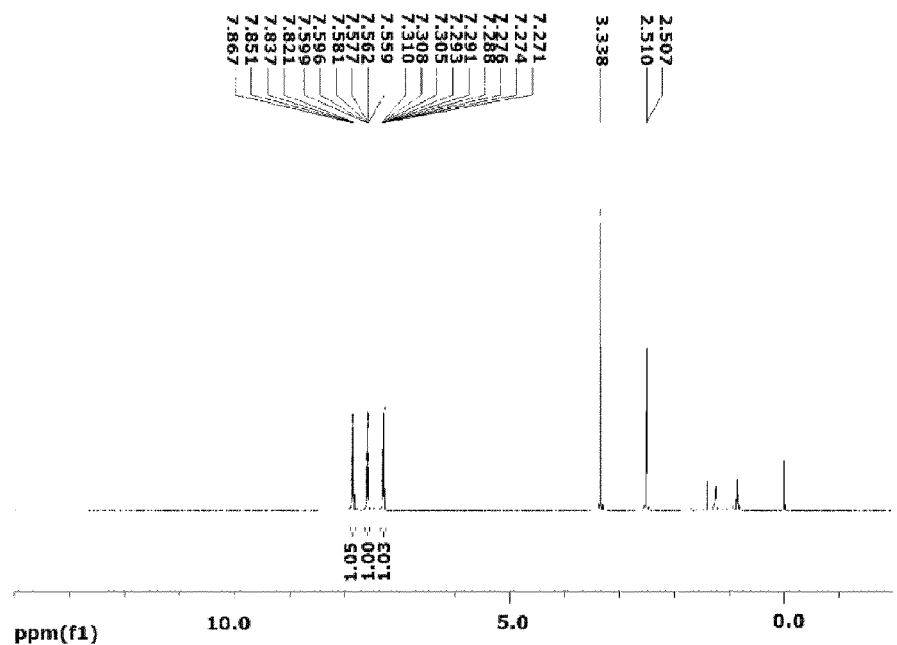
[FIG. 2]
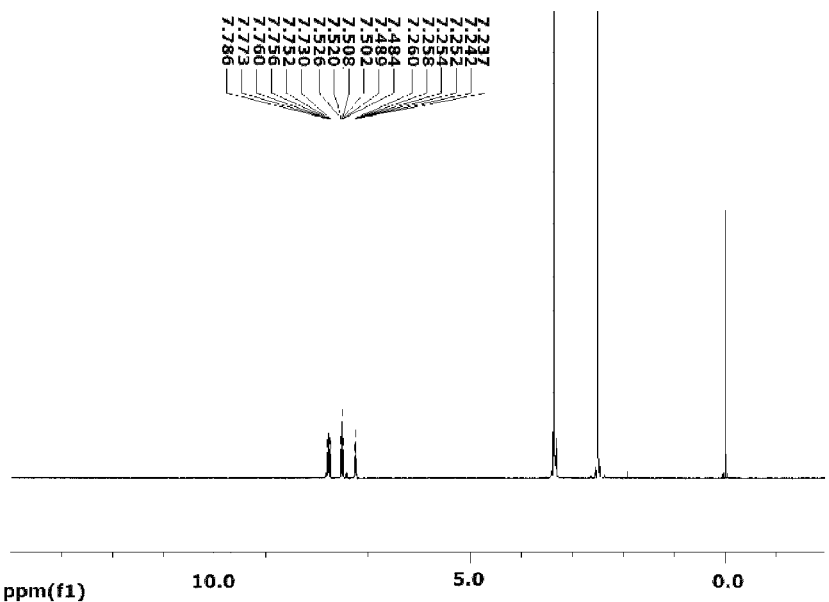

[FIG. 3]
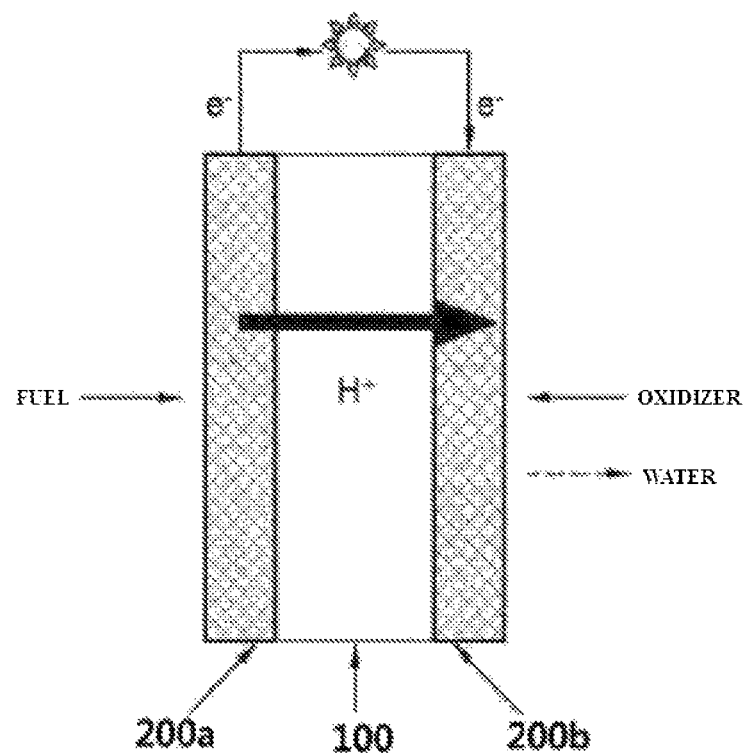

【FIG. 4】
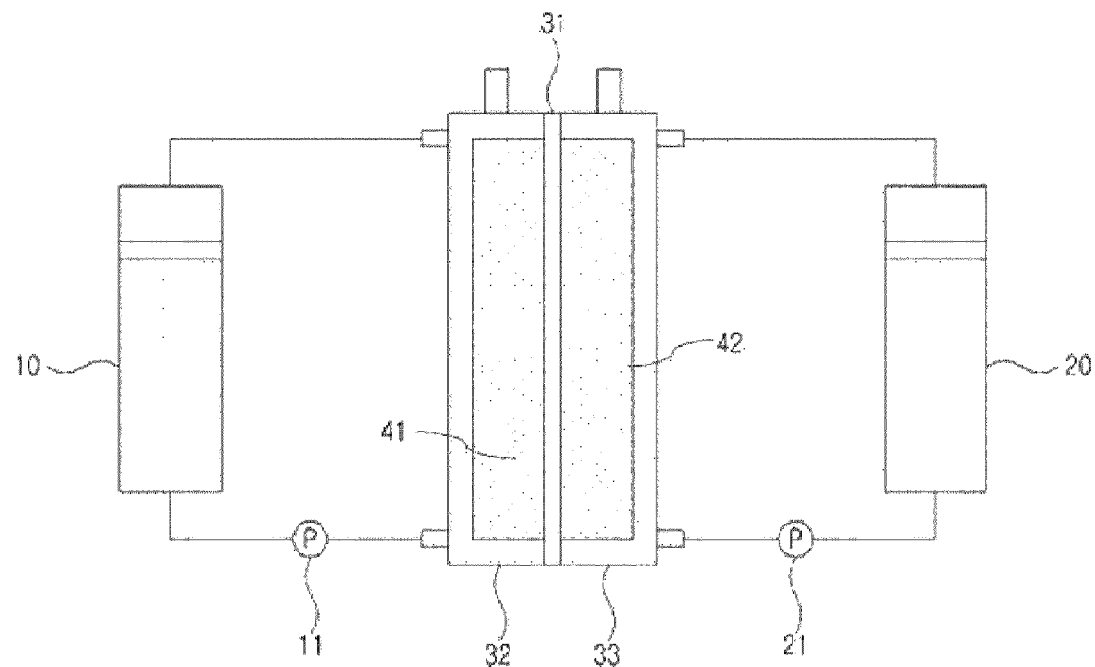
【FIG. 5】
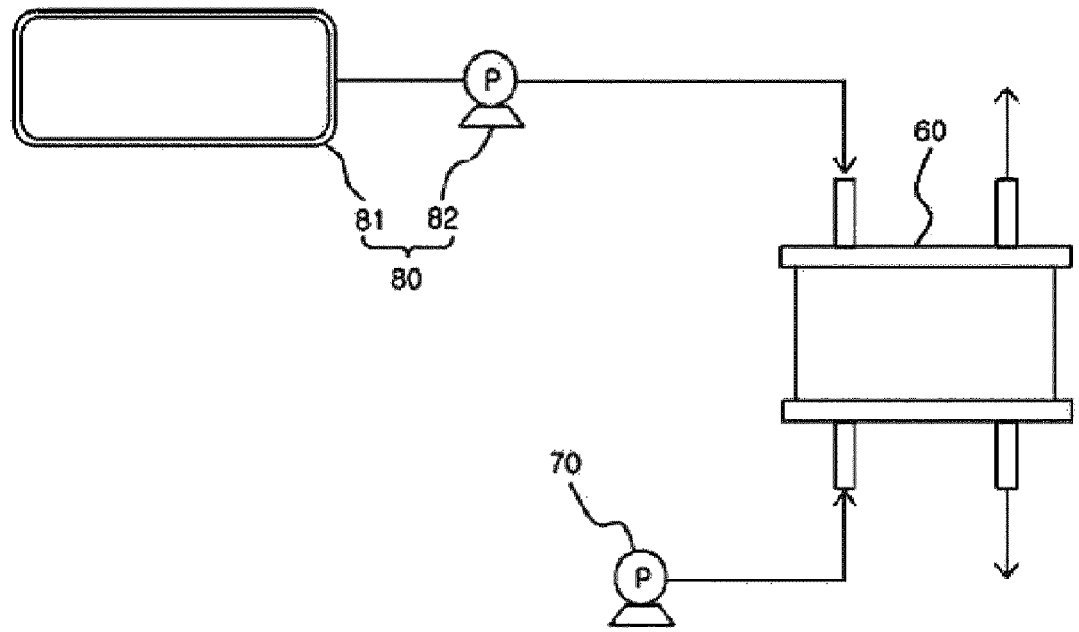

HALOGENATED COMPOUND, POLYMER COMPRISING SAME, AND POLYMER ELECTROLYTE MEMBRANE COMPRISING SAME

TECHNICAL FIELD

The present specification claims priority to and the benefits of Korean Patent Application No. 10-2014-0173157, 10-2014-0173178 and 10-2014-0173137 filed with the Korean Intellectual Property Office on Dec. 4, 2014, and Korean Patent Application No. 10-2015-0170044 filed with the Korean Intellectual Property Office on Dec. 1, 2015, the entire contents of which are incorporated herein by reference.

The present specification relates to a halogenated compound, a polymer including the same and a polymer electrolyte membrane including the same.

BACKGROUND ART

A fuel cell is an energy conversion device directly converting chemical energy of fuel into electric energy. In other words, a fuel cell employs a power generation method utilizing a fuel gas and an oxidizer, and using electrons generated during an oxidation-reduction reaction thereof to produce power. A membrane-electrode assembly (MEA) of a fuel cell is a part where an electrochemical reaction of hydrogen and oxygen occurs, and is formed with a cathode, an anode and an electrolyte membrane, that is, an ion conductive electrolyte membrane.

A redox flow battery (oxidation-reduction flow battery) is a system charged and discharged by active materials included in a liquid electrolyte being oxidized and reduced, and is an electrochemical storage device directly storing chemical energy of the active materials as electric energy. A unit cell of the redox flow battery includes an electrode, an electrolyte and an ion-exchange membrane (electrolyte membrane).

Due to their high energy efficiency and environmental friendly properties of low contaminant emissions, fuel cells and redox flow batteries have been researched and developed as a next generation energy source.

A core constituent in a fuel cell and a redox flow battery is a polymer electrolyte membrane capable of cation exchange, and properties of 1) excellent proton conductivity, 2) preventing an electrolyte crossover, 3) high chemical resistance, 4) strengthening mechanical properties and/or 4) low swelling ratio are favorably required. The polymer electrolyte membrane is divided into fluorine-based, partial fluorine-based, hydrocarbon-based and the like, and a partial fluorine-based polymer electrolyte membrane has advantages of exhibiting excellent physical and chemical stability and high thermal stability by having a fluorine-based main chain. In addition, in the partial fluorine-based polymer electrolyte membrane, a cation transfer functional group is attached at the end of the fluorine-based chain as in a fluorine-based polymer electrolyte membrane, and therefore, advantages of both a hydrocarbon-based polymer electrolyte membrane and a fluorine-based polymer electrolyte membrane are capable of being obtained.

However, a partial fluorine-based polymer electrolyte membrane has a problem in that cation conductivity is relatively low since micro-phase separation and aggregation of a cation transfer functional group are not effectively controlled. Accordingly, researches have been progressed in the direction of securing high cation conductivity through controlling distribution and micro-phase separation of a sulfonic acid group.

PRIOR ART DOCUMENTS

Patent Documents

Korean Patent Application Laid-Open Publication No. 2003-0076057

DISCLOSURE

Technical Problem

The present specification is directed to providing a halogenated compound capable of securing high cation conductivity, a polymer including the same, and a polymer electrolyte membrane including the same.

Technical Solution

One embodiment of the present specification provides a halogenated compound represented by the following Chemical Formula 1.

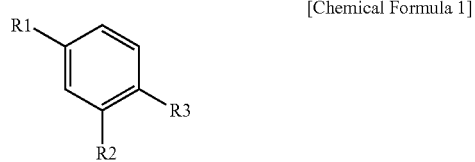

[Chemical Formula 1]

In Chemical Formula 1,
R1 to R3 are the same as or different from each other, and each independently represented by a halogen group; the following Chemical Formula 2; or the following Chemical Formula 3,
at least one of R1 to R3 is a halogen group,
at least one of R1 to R3 is the following Chemical Formula 2,

[Chemical Formula 2]

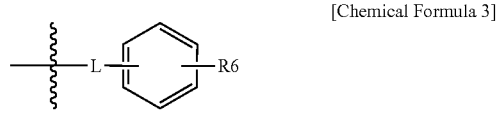

[Chemical Formula 3]

in Chemical Formulae 2 and 3,
A is —$SO_3H$, —$SO_3^-M^+$, —COOH, —$COO^-M^+$, —$PO_3H_2$, —$PO_3H^-M^+$, —$PO_3^{2-}2M^+$, —$O(CF_2)_mSO_3H$, —$O(CF_2)_mSO_3^-M^+$, —$O(CF_2)_mCOOH$, —$O(CF_2)_mCOO^-M^+$, —$O(CF_2)_mPO_3H_2$, —$O(CF_2)_mPO_3H^-M^+$ or —$O(CF_2)_mPO_3^{2-}2M^+$,
m is an integer of 1 to 6,
M is a group 1 element, R4 and R5 are the same as or different from each other, and each independently a halogen group, n is an integer of 2 to 10, and structures in the 2 to 10 parentheses are the same as or different from each other, L is O, S, $SO_2$, CO or $CF_2$, and R6 is a hydroxyl group; or a halogen group.

One embodiment of the present specification provides a polymer including a monomer derived from the halogenated compound described above.

One embodiment of the present specification provides a polymer electrolyte membrane including the polymer.

One embodiment of the present specification provides a reinforced membrane including a substrate; and the polymer.

One embodiment of the present specification provides a membrane-electrode assembly including an anode; a cathode; and the polymer electrolyte membrane described above provided between the anode and the cathode.

One embodiment of the present specification provides a membrane-electrode assembly including an anode; a cathode; and the reinforced membrane described above provided between the anode and the cathode.

One embodiment of the present specification provides a polymer electrolyte-type fuel cell including two or more of the membrane-electrode assemblies described above; a stack including a bipolar plate provided between the membrane-electrode assemblies; a fuel supplying unit supplying fuel to the stack; and an oxidizer supplying unit supplying an oxidizer to the stack.

One embodiment of the present specification provides a redox flow battery including a positive electrode cell including a positive electrode and a positive electrode liquid electrolyte; a negative electrode cell including a negative electrode and a negative electrode liquid electrolyte; and the polymer electrolyte membrane described above provided between the positive electrode cell and the negative electrode cell.

Lastly, one embodiment of the present specification provides a redox flow battery including a positive electrode cell including a positive electrode and a positive electrode liquid electrolyte; a negative electrode cell including a negative electrode and a negative electrode liquid electrolyte; and the reinforced membrane described above provided between the positive electrode cell and the negative electrode cell.

Advantageous Effects

A halogenated compound according to one embodiment of the present specification can be used as a monomer of a polymer. When using the compound as a monomer, reactivity is enhanced during polymerization, which is advantageous in obtaining a high molecular weight polymer, and the polymer including the monomer can be stable.

A polymer electrolyte membrane including the polymer according to one embodiment of the present specification readily forms a hydrophilic-hydrophobic phase separation structure.

In addition, by controlling the phase separation structure, the polymer electrolyte membrane efficiently forms a hydrophilic channel in the polymer electrolyte membrane.

The polymer electrolyte membrane also has excellent proton conductivity. As a result, high performance of a fuel cell and/or a redox flow battery including the same is obtained.

A redox flow battery including a reinforced membrane according to one embodiment of the present specification is capable of reducing a vanadium ion crossover.

Lastly, when including a reinforced membrane according to one embodiment of the present specification, durability is enhanced, and a device having a long lifespan can be provided.

DESCRIPTION OF DRAWINGS

FIG. 1 is a diagram showing an NMR graph of Chemical Formula A-1.

FIG. 2 is a diagram showing an NMR graph of Chemical Formula 1-1.

FIG. 3 is a schematic diagram showing a principle of electricity generation of a fuel cell.

FIG. 4 is a diagram schematically illustrating one embodiment of a redox flow battery.

FIG. 5 is a diagram schematically illustrating one embodiment of a fuel cell.

REFERENCE NUMERAL

100: Electrolyte Membrane
200a: Anode
200b: Cathode
10, 20: Tank
11, 21: Pump
31: Electrolyte Membrane
32: Positive Electrode Cell
33: Negative Electrode Cell
41: Positive Electrode Liquid Electrolyte
42: Negative Electrode Liquid Electrolyte
60: Stack
70: Oxidizer Supplying Unit
80: Fuel Supplying Unit
81: Fuel Tank
82: Pump

MODE FOR DISCLOSURE

Hereinafter, the present specification will be described in more detail.

In the present specification, a description of a certain part "including" certain constituents means capable of further including other constituents, and does not exclude other constituents unless particularly stated on the contrary.

One embodiment of the present specification provides a halogenated compound represented by Chemical Formula 1.

In one embodiment of the present specification, the halogenated compound may be used as a monomer in a polymer. Specifically, an S atom is used as a linker of a —$[CR4R5]_n$-A structure in Chemical Formula 2 and a benzene ring of Chemical Formula 1. In this case, an electron withdrawing character of the —$[CR4R5]_n$-A linked by the S atom allows the halogenated compound to be used as a monomer having favorable reactivity in a polymer synthesis reaction.

In one embodiment of the present specification, R1 and R2 are the same as or different from each other, and each independently a halogen group. Specifically, R1 and R2 may be each independently selected from the group consisting of F; Cl; Br; and I.

In one embodiment of the present specification, at least one of R1 to R3 is a halogen group, and at least one thereof is Chemical Formula 2.

In one embodiment of the present specification, two of R1 to R3 are a halogen group, and one thereof is Chemical Formula 2.

In one embodiment of the present specification, R1 and R2 are the same as or different from each other, and each independently a halogen group, and R3 is Chemical Formula 2. In one embodiment of the present specification, R1 and R2 are fluorine, and R3 is Chemical Formula 2.

In one embodiment of the present specification, n is an integer of 2 to 10. In another embodiment of the present specification, n is an integer of 2 to 6.

In a monomer derived from the halogenated compound of Chemical Formula 1 according to one embodiment of the present specification, the number of n may be controlled. In this case, a length of the structure in the parenthesis may be controlled, or a mass of a polymer may be controlled.

In one embodiment of the present specification, n is 2.
In another embodiment, n is 3.
In another embodiment, n is 4.
In another embodiment, n is 5.
In another embodiment, n is 6.
In another embodiment, n is 7.
In one embodiment of the present specification, n is 8.
In another embodiment, n is 9.
In one embodiment of the present specification, n is 10.

In one embodiment of the present specification, A is $-SO_3H$ or $-SO_3^-M^+$.

In another embodiment, A is $-SO_3H$.

As above, when A is $-SO_3H$ or $-SO_3^-M^+$ in Chemical Formula 2, a chemically stable polymer may be formed.

In one embodiment of the present specification, M is a group 1 element.

In the present specification, the group 1 element may be Li, Na or K.

In another embodiment, R4 and R5 are the same as or different from each other, and each independently a halogen group. Specifically, R4 and R5 may be each independently selected from the group consisting of F; Cl; Br; and I.

When a polymer including a monomer derived from the halogenated compound according to one embodiment of the present specification is included in a polymer electrolyte membrane and R4 and R5 of Chemical Formula 2 are a halogen group, there is an advantage in that electrons are favorably attracted increasing acidity of the A functional group at the end and thereby facilitating hydrogen ion migration, and the structure of the polymer electrolyte membrane is strengthened. Specifically, according to one embodiment of the present specification, the advantage may be maximized when R4 and R5 are fluorine.

In one embodiment of the present specification, the halogenated compound represented by Chemical Formula 1 may be represented by any one of the following Chemical Formulae 1-1 to 1-9.

[Chemical Formula 1-1]
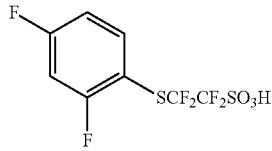

[Chemical Formula 1-2]
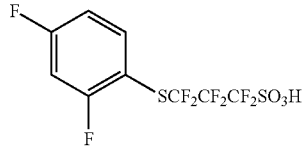

[Chemical Formula 1-3]
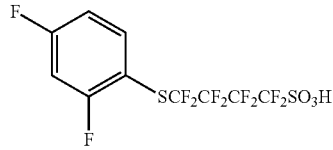

[Chemical Formula 1-4]
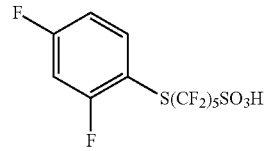

[Chemical Formula 1-5]
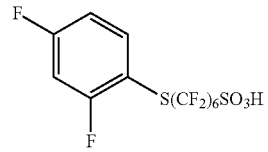

[Chemical Formula 1-6]
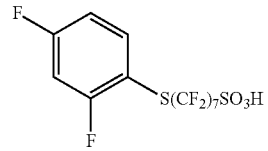

[Chemical Formula 1-7]
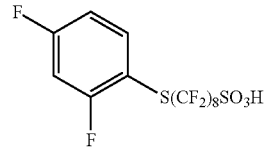

[Chemical Formula 1-8]
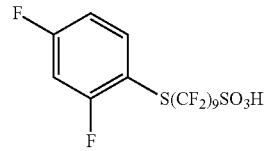

[Chemical Formula 1-9]
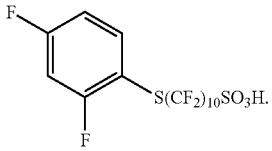

In one embodiment of the present specification, the structure represented by Chemical Formula 3 is represented by the following Chemical Formula 3-1 or Chemical Formula 3-2.

[Chemical Formula 3-1]
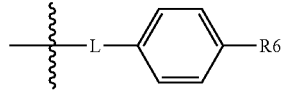

[Chemical Formula 3-2]
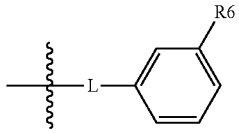

In Chemical Formulae 3-1 and Chemical Formula 3-2, definitions of L and R6 are the same as in Chemical Formula 3.

In one embodiment of the present specification, one of R1 to R3 is a halogen group, another is Chemical Formula 2, and the remaining one is Chemical Formula 3.

In another embodiment of the present specification, R1 is Chemical Formula 3-1, R2 is Chemical Formula 2, and L is CO; $CF_2$; or $SO_2$.

In another embodiment, R1 is Chemical Formula 3-2, R3 is Chemical Formula 2, and L is S; or O.

In addition, when L is CO, $CF_2$ or $SO_2$ as in one embodiment of the present specification, Chemical Formula 3-1 having R6 at a para position has more superior reactivity.

When L is S; or O as in one embodiment of the present specification, Chemical Formula 3-2 having R6 at a meta position may have more superior reactivity due to an electron donating effect.

When including Chemical Formula 3, stability may be further enhanced when controlling the position of —[CR4R5]$_n$-A linked by an S atom of Chemical Formula 2 depending on the properties of L.

In one embodiment of the present specification, the compound represented by Chemical Formula 1 is represented by any one of the following Chemical Formulae 1-10 to 1-15.

[Chemical Formula 1-10]

$SCF_2CF_2SO_3H$

[Chemical Formula 1-11]

$SCF_2CF_2SO_3H$

[Chemical Formula 1-12]

$SCF_2CF_2SO_3H$

[Chemical Formula 1-13]

$SCF_2CF_2SO_3H$

[Chemical Formula 1-14]

$SCF_2CF_2SO_3H$

[Chemical Formula 1-15]

$SCF_2CF_2SO_3H$.

The compound according to one embodiment of the present specification may be prepared by introducing a —[CR4R5]$_n$-structure of which both ends are brominated to a benzene ring substituted with a halogen group and a thiol group, and then oxidizing the compound substituting A with hydrogen peroxide by reacting sodium hydrosulfite ($Na_2S_2O_4$) and sodium bicarbonate, however, the method is not limited thereto.

One embodiment of the present specification provides a polymer including a monomer derived from the halogenated compound.

In the present specification, the "derived" means producing new bonds as bonds of a compound are cut or substituents fall off, and the unit derived from the compound may mean a unit linked to a main chain of a polymer. The unit may form a polymer by being included in a main chain of the polymer.

In one embodiment of the present specification, when two of R1 to R3 are a halogen group, a polymer may be formed by bonding in the polymer as the two halogen groups fall off. In another embodiment, when one of R1 to R3 is a halogen group, a polymer may be formed by bonding in the polymer as the one halogen group and R6 of Chemical Formula 3 fall off.

In one embodiment of the present specification, the monomer derived from the halogenated compound represented by Chemical Formula 1 may be represented by monomers of the following Chemical Formula 1-A to Chemical Formula 1-C.

[Chemical Formula 1-A]

[Chemical Formula 1-B]

[Chemical Formula 1-C]

In Chemical Formulae 1-A to Chemical Formula 1-C, definitions of L, R4, R5, A and n are the same as above.

In one embodiment of the present specification, a polymer including the unit of Chemical Formula 1-A is more preferred in terms of polymer formation and ion conductivity.

In one embodiment of the present specification, the monomer represented by Chemical Formula 1-A is represented by any one of the following Chemical Formulae 1-A-1 to 1-A-9.

[Chemical Formula 1-A-1]

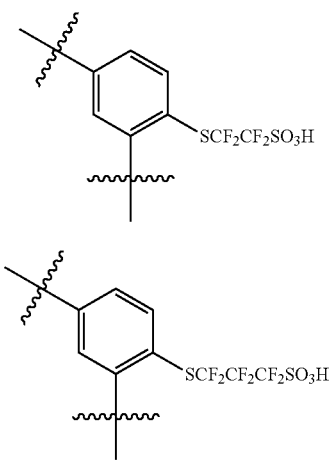

[Chemical Formula 1-A-2]

[Chemical Formula 1-A-3]

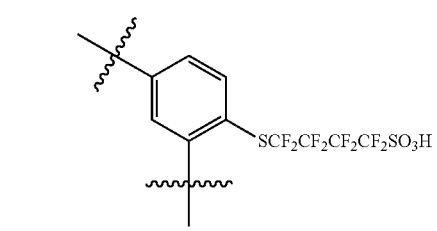

[Chemical Formula 1-A-4]

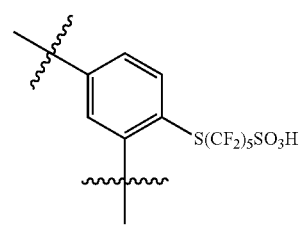

[Chemical Formula 1-A-5]

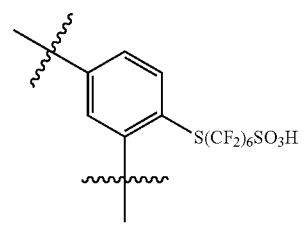

[Chemical Formula 1-A-6]

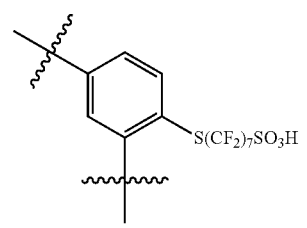

[Chemical Formula 1-A-7]

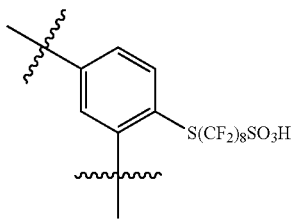

[Chemical Formula 1-A-8]

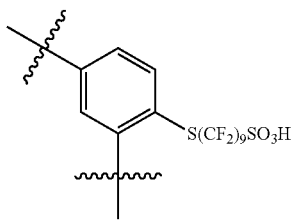

[Chemical Formula 1-A-9]

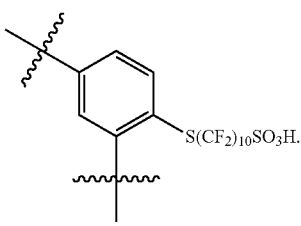

In one embodiment of the present specification, the monomer represented by Chemical Formula 1-B is represented by any one of the following Chemical Formulae 1-B-1 to 1-B-3.

[Chemical Formula 1-B-1]

[Chemical Formula 1-B-2]

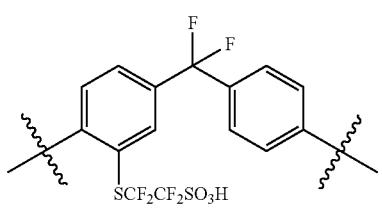

[Chemical Formula 1-B-3]

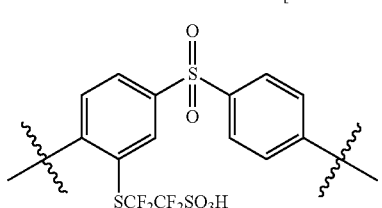

In another embodiment, the monomer represented by Chemical Formula 1-C is represented by any one of the following Chemical Formulae 1-C-1 to 1-C-3.

[Chemical Formula 1-C-1]

[Chemical Formula 1-C-2]

[Chemical Formula 1-C-3]

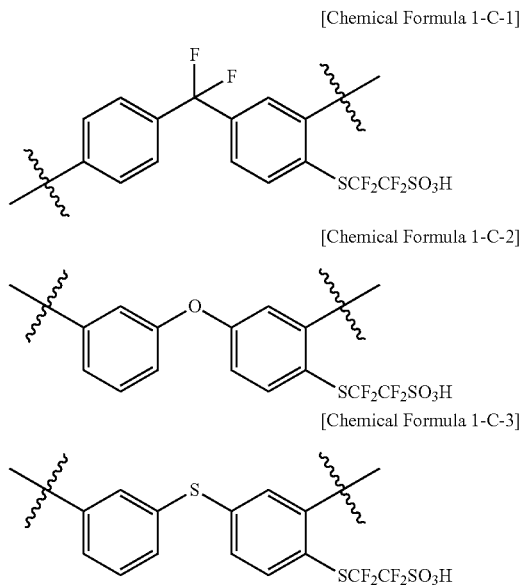

In the present specification,

means binding to adjacent substituents or a main chain of a polymer.

In one embodiment of the present specification, the polymer includes the unit represented by Chemical Formula 1 in 1 mol % to 100 mol %. Specifically, in one embodiment of the present specification, the polymer includes only the unit represented by Chemical Formula 1. In another embodiment, the polymer may further include may further include a different second unit in addition to the unit represented by Chemical Formula 1. In one embodiment of the present specification, when the polymer further includes a second unit, the content of the unit represented by Chemical Formula 1 is preferably from 5 mol % to 65 mol %.

The unit represented by Chemical Formula 1 according to one embodiment of the present specification performs a role of controlling ion conductivity of a separator.

The second unit according to another embodiment may be selected from among units enhancing mechanical strength of the polymer, and the type is not limited as long as it is a unit capable of enhancing mechanical strength.

In the unit represented by Chemical Formulae 1-A to 1-C according to one embodiment of the present specification, functional groups including a partial fluorine-based stretch out in a pendant form, and therefore, phase separation is readily achieved since partial fluorine-based functional groups in the polymer are favorably aggregated. Accordingly, ion channels are readily formed and ions are selectively exchanged enhancing ion conductivity of a separator.

In one embodiment of the present specification, the polymer is a block polymer including a hydrophilic block; and a hydrophobic block, and the hydrophilic block includes a monomer derived from the halogenated compound.

In the present specification, the block polymer means a polymer formed by one block, and one, two or more blocks that are different from the one block being linked to each other by a polymer main chain.

In one embodiment of the present specification, the block polymer may include a hydrophilic block and a hydrophobic block. Specifically, in one embodiment, the block polymer may include a hydrophilic block including the first unit, and a hydrophobic block.

The "hydrophilic block" of the present specification means a block having an ion-exchange group as a functional group. Herein, the functional group may be at least any one selected from the group consisting of $-SO_3H$, $-SO_3^-M^-$, $-COOH$, $-COO^-M^-$, $-PO_3H^-M^+$, $-PO_3^{2-}2M^+$, $-O(CF_2)_mSO_3H$, $-O(CF_2)_mSO_3^-M^+$, $-O(CF_2)_mCOOH$, $-O(CF_2)_mCOO^-M^+$, $-O(CF_2)_mPO_3H_2$, $-O(CF_2)_mPO_3H^-M^+$ and $-O(CF_2)_mPO_3^{2-}2M^+$. Herein, M may be a metallic element. In other words, the functional group may be hydrophilic.

The halogenated compound according to one embodiment of the present specification may exhibit hydrophilicity by including the functional group of A.

The "block having an ion-exchange group" of the present specification means a block including an average of 0.5 or more ion-exchange groups when representing as the number of ion-exchange groups per one structure unit forming the corresponding block, and including an average of 1.0 or more ion-exchange groups per one structure unit is more preferred.

The "hydrophobic block" of the present specification means the polymer block that does not substantially has an ion-exchange group.

The "block that does not substantially include an ion-exchange group" of the present specification means a block including an average of less than 0.1 ion-exchange groups when representing as the number of ion-exchange groups per one structure unit forming the corresponding block, and including an average of 0.05 or less is more preferred, and a block that does not include an ion-exchange group at all is even more preferred.

According to an embodiment of the present specification, the hydrophilic block and the hydrophobic block are clearly divided and separated in the block polymer and phase separation is readily obtained, and therefore, ions are readily transferred. According to one embodiment of the present specification, the hydrophilic block and the hydrophobic block are more clearly divided when including a monomer derived from the halogenated compound, and an ion transfer effect may be more superior compared to existing polymers.

In one embodiment of the present specification, the hydrophilic block and the hydrophobic block are included in a ratio of 1:0.1 to 1:10 in the block polymer. In one embodiment of the present specification, the hydrophilic block and the hydrophobic block are included in a ratio of 1:0.1 to 1:2 in the block polymer.

In this case, an ion transfer ability of the block polymer may be enhanced.

In one embodiment of the present specification, a monomer derived from the halogenated compound is included in 0.01 mol % to 100 mol % in the hydrophilic block based on the hydrophilic block.

In one embodiment of the present specification, the hydrophilic block has a number average molecular weight of 1,000 g/mol to 300,000 g/mol. In a specific embodiment, the number average molecular weight is from 2,000 g/mol to 100,000 g/mol. In another embodiment, the number average molecular weight is from 2,500 g/mol to 50,000 g/mol.

In one embodiment of the present specification, the hydrophobic block has a number average molecular weight of 1,000 g/mol to 300,000 g/mol. In a specific embodiment, the number average molecular weight is from 2,000 g/mol to 100,000 g/mol. In another embodiment, the number average molecular weight is from 2,500 g/mol to 50,000 g/mol.

In one embodiment of the present specification, the polymer further includes a brancher. The brancher in the present specification performs a role of linking or crosslinking polymer chains.

In one embodiment of the present specification, the block polymer further includes a brancher.

In the polymer further including a brancher in the present specification, the brancher may directly form a main chain of the polymer, and a mechanical degree of integration of a thin membrane may be enhanced. Specifically, in the branched polymer of the present disclosure, the brancher directly forms a main chain of the polymer without carrying out a post-sulfonation reaction or a cross-linking reaction of a sulfonated polymer by polymerizing branched hydrophobic blocks that do not include acid substituents and branched hydrophilic blocks that include acid substituents, and the hydrophobic blocks maintaining a mechanical degree of integration of a thin membrane and the hydrophilic blocks providing ion conductivity to the thin membrane are alternately linked through chemical bonds.

In one embodiment of the present specification, the polymer further includes a brancher derived from a compound represented by the following Chemical Formula 4; or a brancher represented by the following Chemical Formula 5.

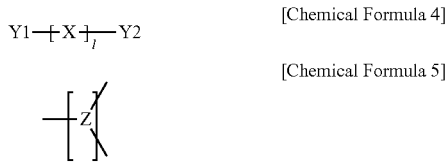

[Chemical Formula 4]

[Chemical Formula 5]

In Chemical Formulae 4 and 5,

X is S; O; CO; SO; $SO_2$; NR; a hydrocarbon-based or fluorine-based assembly, l is an integer of 0 to 10, when l is 2 or greater, two or more Xs are the same as or different from each other, Y1 and Y2 are the same as or different from each other, and each independently NRR; an aromatic ring in which one, two or more are substituted with substituents selected from the group consisting of a hydroxyl group and a halogen group; or an aliphatic ring in which one, two or more are substituted with substituents selected from the group consisting of a hydroxyl group and a halogen group, R is an aromatic ring substituted with a halogen group; or an aliphatic ring substituted with a halogen group, and Z is a trivalent organic group.

In an embodiment of the present specification, the brancher derived from the compound of Chemical Formula 4 may function as a brancher as, in each of Y1 and Y2 that are an aromatic ring substituted with a halogen group; or an aliphatic ring substituted with a halogen group, the halogen group falls off from the aromatic ring or the aliphatic ring. Specifically, the brancher derived from the compound of Chemical Formula 4 in the present specification may function as a brancher in the polymer as two or more halogen groups fall off.

Examples of the substituents of the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the hydrocarbon-based means an organic compound formed only with carbon and hydrogen, and includes linear, branched, cyclic hydrocarbon and the like, but is not limited thereto. In addition, a single bond, a double bond or a triple bond may be included, however, the hydrocarbon-based is not limited thereto.

In the present specification, a fluorine-based assembly means a part or all of carbon-hydrogen bonds in the hydrocarbon-based are substituted with fluorine.

In the present specification, the aromatic ring may be an aromatic hydrocarbon ring or an aromatic heteroring, and may be monocyclic or multicyclic.

Specifically, examples of the aromatic hydrocarbon ring may include a monocyclic aromatic group such as a phenyl group, a biphenyl group and a terphenyl group, and a multicyclic aromatic group such as a naphthyl group, a binaphthyl group, an anthracenyl group, a phenanthrenyl group, a pyrenyl group, a perylenyl group, a tetracenyl group, a chrysenyl group, a fluorenyl group, an acenaphthacenyl group, a triphenylene group and a fluoranthene group, but are not limited thereto.

In the present specification, the aromatic heteroring means a structure including one or more heteroatoms such as O, S, N and Se instead of a carbon atom in the aromatic hydrocarbon ring. Specific examples thereof may include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, the aliphatic ring may be an aliphatic hydrocarbon ring or an aliphatic heteroring, and may be monocyclic or multicyclic. Examples of the aliphatic ring may include a cyclopentyl group, a cyclohexyl group and the like, but are not limited thereto.

In the present specification, the organic group may include an alkyl group, an alkenyl group, a cycloalkyl group, a cycloalkenyl group, an aryl group, an aralkyl group and the like. This organic group may include bonds or substituents in addition to a hydrocarbon group such as heteroatoms in the organic group. In addition, the organic group may be any of linear, branched or cyclic.

In the present specification, the trivalent organic group means a trivalent group having 3 binding sites in an organic compound.

In addition, the organic group may form a cyclic structure, and may form bonds including heteroatoms as long as it does not harm effects of the present disclosure.

Specifically, bonds including heteroatoms such as an oxygen atom, a nitrogen atom and a silicon atom may be included. Specific examples thereof may include ether bonds, thioether bonds, carbonyl bonds, thiocarbonyl bonds, ester bonds, amide bonds, urethane bonds, imino bonds (—N=C(-A)-, —C(=NA)-: A represents a hydrogen atom or an organic group), carbonate bonds, sulfonyl bonds, sulfinyl bonds, azo bonds and the like, but are not limited thereto.

Examples of the cyclic structure may include the aromatic ring, the aliphatic ring and the like described above, and the cyclic structure may be monocyclic or multicyclic.

In the present specification, the alkyl group may be linear or branched, and although not particularly limited thereto, the number of carbon atoms is preferably from 1 to 50. Specific examples thereof may include a methyl group, an ethyl group, a propyl group, an isopropyl group, a butyl group, a t-butyl group, a pentyl group, a hexyl group, a heptyl group and the like, but are not limited thereto.

In the present specification, the alkenyl group may be linear or branched, and although not particularly limited thereto, the number of carbon atoms is preferably from 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and particularly, may include a cyclopentyl group, a cyclohexyl group and the like, but is not limited thereto.

In one embodiment of the present specification, l is 3 or greater.

In one embodiment of the present specification, X is S.

In another embodiment, X is a haloalkyl group.

In another embodiment, X is $CH_2$.

In another embodiment of the present specification, X is NR.

In one embodiment of the present specification, Y1 and Y2 are the same as or different from each other, and each independently a halogen-substituted aromatic ring.

In one embodiment of the present specification, Y1 and Y2 are the same as or different from each other, and each independently a fluorine-substituted aromatic hydrocarbon ring.

In one embodiment of the present specification, Y1 and Y2 are the same as or different from each other, and each independently NRR.

In another embodiment, Y1 and Y2 are each a fluorine-substituted phenyl group. Specifically, 2,4-phenyl, 2,6-phenyl, 2,3-phenyl, 3,4-phenyl and the like are included, however, Y1 and Y2 are not limited thereto.

In one embodiment of the present specification, the compound represented by Chemical Formula 4 may be represented by any one of the following structures.

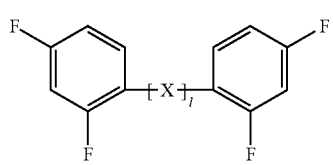

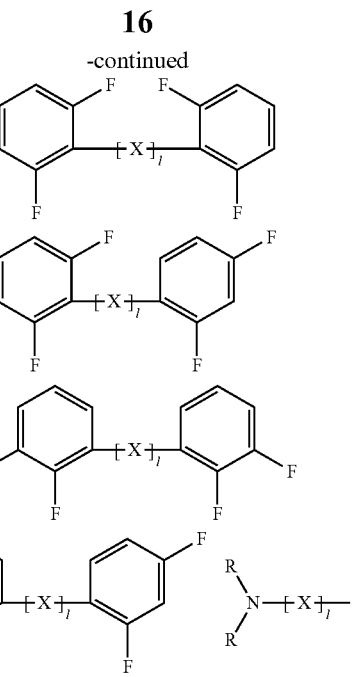

In the structures, definitions of X, 1 and R are the same as in Chemical Formula 4.

According to one embodiment of the present specification, Z in Chemical Formula 5 may be represented by any one of the following Chemical Formulae 5-1 to 5-4.

[ Chemical Formula 5-1]

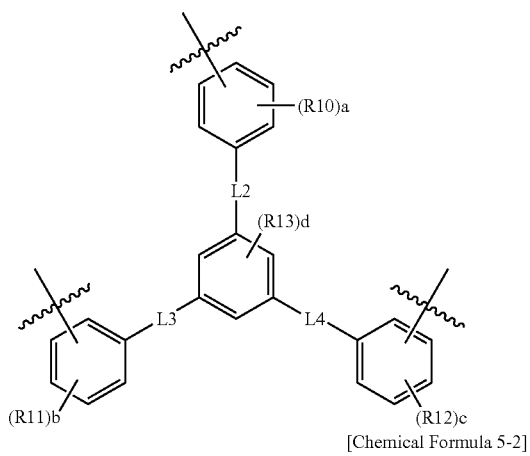

[Chemical Formula 5-2]

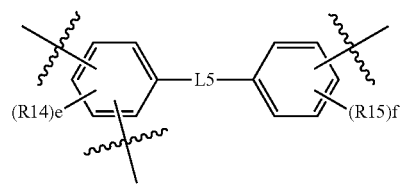

[Chemical Formula 5-3]

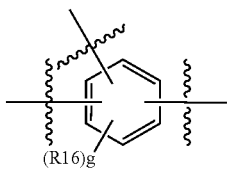

[Chemical Formula 5-4]

In Chemical Formulae 5-1 to 5-4,

L2 to L8 are the same as or different from each other, and each independently a direct bond; —S—; —O—; —CO—; or —SO$_2$—, R10 to R20 are the same as or different from each other, and each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heteroaryl group, a, b, c, f, h, i and j are each an integer of 1 to 4, d, e and g are each an integer of 1 to 3, k is an integer of 1 to 6, and when a, b, c, d, e, f, g, h, i, j and k are each an integer of 2 or greater, structures in the two or more parentheses are the same as or different from each other.

In one embodiment of the present specification, L1 is CO.

In another embodiment, L1 is SO$_2$.

In another embodiment, L1 is S.

In another embodiment, L2 is CO.

In another embodiment, L2 is SO$_2$.

In another embodiment, L2 is S.

In one embodiment of the present specification, L3 is CO.

In another embodiment, L3 is SO$_2$.

In another embodiment, L3 is S.

In one embodiment of the present specification, L4 is CO.

In another embodiment, L4 is SO$_2$.

In one embodiment of the present specification, L5 is a direct bond.

In another embodiment, L6 is a direct bond.

In one embodiment of the present specification, L7 is a direct bond.

In one embodiment of the present specification, R10 to R20 are hydrogen.

In one embodiment of the present specification, R16 is a halogen group.

In another embodiment, R16 is fluorine.

In addition, in one embodiment of the present specification, the brancher represented by Chemical Formula 5 may be represented by any one of the following structures.

-continued

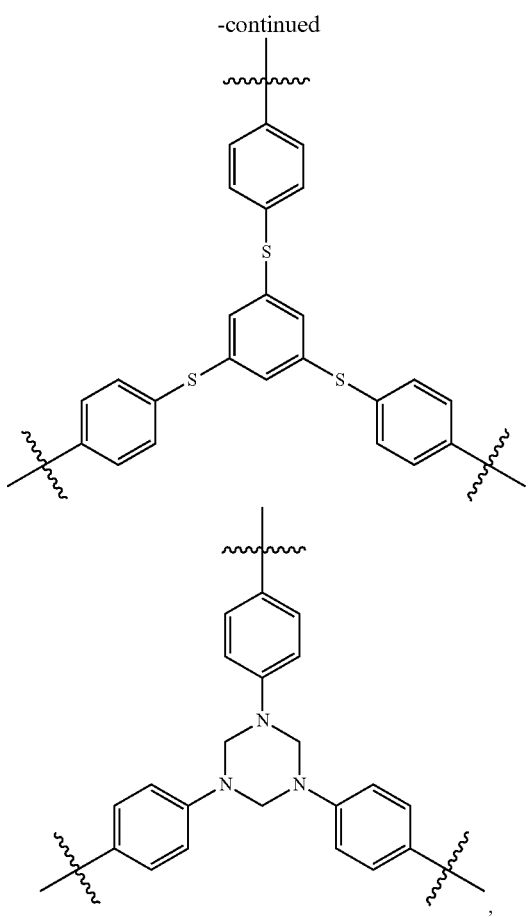

In one embodiment of the present specification, the polymer has a weight average molecular weight of 500 g/mol to 5,000,000 g/mol. When the polymer has a weight average molecular weight in the above-mentioned range, mechanical properties of an electrolyte membrane including the polymer do not decline, and proper polymer solubility is maintained, and therefore, the electrolyte membrane may be readily prepared.

In addition, one embodiment of the present specification provides a polymer electrolyte membrane including the polymer described above.

When including a polymer including a monomer derived from the halogenated compound according to one embodiment of the present specification, high mechanical strength and high ion conductivity are obtained, and phase separation of the electrolyte membrane may be readily accomplished.

In the present specification, the "electrolyte membrane" is a membrane capable of exchanging ions, and includes a membrane, an ion-exchange membrane, an ion-transfer membrane, an ion-conductive membrane, a separator, an ion-exchange separator, an ion-transfer separator, an ion-conductive separator, an ion-exchange electrolyte membrane, an ion-transfer electrolyte membrane, an ion-conductive electrolyte membrane or the like.

The polymer electrolyte membrane according to one embodiment of the present specification may be prepared using materials and/or methods known in the art except for including a polymer including a monomer derived from the halogenated compound.

According to one embodiment of the present specification, the polymer electrolyte membrane has ion conductivity of 0.01 S/cm to 0.5 S/cm. In another embodiment, the polymer electrolyte membrane has ion conductivity of greater than or equal to 0.01 S/cm and less than or equal to 0.3 S/cm.

In one embodiment of the present specification, ion conductivity of the polymer electrolyte membrane may be measured under a humidity condition. A humidity condition in the present specification may mean relative humidity (RH) of 10% to 100%.

In addition, in one embodiment of the present specification, the polymer electrolyte membrane has an ion exchange capacity (IEC) value of 0.01 mmol/g to 5 mmol/g. When the polymer electrolyte membrane has an ion exchange capacity value in the above-mentioned range, ion channels are formed in the polymer electrolyte membrane, and the polymer may exhibit ion conductivity.

In one embodiment of the present specification, the polymer electrolyte membrane has a thickness of 1 μm to 500 μm. The polymer electrolyte membrane having the above-mentioned thickness range reduces electric short and electrolyte material crossover, and may exhibit an excellent cation conductivity property.

One embodiment of the present specification provides a reinforced membrane including a substrate; and the polymer described above.

In one embodiment of the present specification, the 'reinforced membrane' is an electrolyte membrane including a substrate, a reinforcing material, as a membrane capable of exchanging ions, and may mean a substrate-including membrane, ion-exchange membrane, ion-transfer membrane, ion-conductive membrane, separator, ion-exchange separator, ion-transfer separator, ion-conductive separator, ion-exchange electrolyte membrane, ion-transfer electrolyte membrane, ion-conductive electrolyte membrane or the like.

In the present specification, the substrate may mean a support having a three-dimensional network structure, and the reinforced membrane including the substrate and the polymer may mean the polymer being included in at least a part of one surface of the substrate, a surface opposite to the one surface and a pore region inside the substrate. In other words, the reinforced membrane of the present specification may be provided in a form of the polymer being impregnated in the substrate.

The polymer is the same as described above.

Hydrocarbon-based ion-transfer separators have problems in that an ion transfer ability is inferior compared to fluorine-based separators, and chemical resistance is weak. Accordingly, by including a polymer including the unit represented by Chemical Formula 1, the reinforced membrane according to one embodiment of the present specification has high mechanical strength and high ion conductivity, and phase separation of the reinforced membrane may be readily accomplished.

In addition, by including the substrate, the reinforced membrane according to one embodiment of the present specification enhances chemical resistance and durability, and thereby enhances a lifespan of a device.

In one embodiment of the present specification, one or two types from the group consisting of polypropylene (PP), polytetrafluoroethylene (PTFE), polyethylene (PE) and polyvinylidene fluoride (PVDF) are selected as the substrate.

In one embodiment of the present specification, the content of the polymer is from 10 parts by weight to 99 parts by weight with respect to 100 parts by weight of the reinforced membrane.

In another embodiment, the content of the polymer is from 10 parts by weight to 99 parts by weight and the content of the substrate is from 1 part by weight to 90 parts by weight, with respect to 100 parts by weight of the reinforced membrane. As the content of the substrate increases, a vanadium ion crossover may be reduced, and as the content of the polymer increases, battery performance may be enhanced.

Accordingly, when the content of the substrate and the polymer according to one embodiment of the present specification is in the above-mentioned range, a vanadium ion crossover may be reduced while maintaining battery performance.

According to one embodiment of the present specification, the reinforced membrane has ion conductivity of greater than or equal to 0.001 S/cm and less than or equal to 0.5 S/cm. In another embodiment, the reinforced membrane has ion conductivity of greater than or equal to 0.001 S/cm and less than or equal to 0.3 S/cm.

In the present specification, ion conductivity may be measured under the same condition as described above.

In addition, in one embodiment of the present specification, the reinforced membrane has an ion exchange capacity (IEC) value of 0.01 mmol/g to 5.0 mmol/g. When the reinforced membrane has an ion exchange capacity value in the above-mentioned range, ion channels are formed in the reinforced membrane, and the polymer may exhibit ion conductivity.

In one embodiment of the present specification, the reinforced membrane has a thickness of 0.01 μm to 10,000 μm. The reinforced membrane having the above-mentioned thickness range reduces electric short and electrolyte material crossover, and may exhibit an excellent cation conductivity property.

One embodiment of the present specification also provides a method for preparing a reinforced membrane including preparing a substrate; and impregnating the substrate into a polymer including the unit represented by Chemical Formula 1.

In the present specification, impregnation means a polymer infiltrating into a substrate. The impregnation in the present specification may be carried out by dipping the substrate into the polymer, slot die coating, bar casting and the like.

In the present specification, dipping may be expressed by terms such as dip coating or dipping method.

In one embodiment of the present specification, the reinforced membrane may have directivity. Specifically, in one embodiment of the present specification, the substrate may be prepared through monoaxial orientation or biaxial orientation, and directivity of the substrate obtained by the orientation may determine directivity of the reinforced membrane. Therefore, the reinforced membrane according to one embodiment of the present specification may have directivity in a machine direction (MD) and in a direction perpendicular to the machine direction (MD), and the reinforced membrane may exhibit differences in the physical properties such as stress and elongation depending on the directivity.

One embodiment of the present specification also provides a method for preparing a reinforced membrane including preparing a substrate; and dipping the substrate into the polymer.

In the present specification, the substrate and the polymer are the same as described above.

One embodiment of the present specification also provides a membrane-electrode assembly including an anode; a cathode; and the polymer electrolyte membrane described above provided between the anode and the cathode.

One embodiment of the present specification also provides a membrane-electrode assembly including an anode; a cathode; and the reinforced membrane described above provided between the anode and the cathode.

The membrane-electrode assembly (MEA) means an assembly of electrodes (cathode and anode) in which an electrochemical catalyst reaction of fuel and air occurs and a polymer membrane in which hydrogen ion transfer occurs, and is a single assembled unit in which electrodes (cathode and anode) and an electrolyte membrane are adhered.

The membrane-electrode assembly of the present specification has a form of a catalyst layer of an anode and a catalyst layer of a cathode being brought into contact with an electrolyte membrane, and may be prepared using common methods known in the art. As one example, the membrane-electrode assembly may be prepared through thermocompressing the cathode; the anode; and the electrolyte membrane located between the cathode and the anode at 100° C. to 400° C. while sticking these together.

The anode electrode may include an anode catalyst layer and an anode gas diffusion layer. The anode gas diffusion layer may again include an anode micropore layer and an anode electrode substrate.

The cathode electrode may include a cathode catalyst layer and a cathode gas diffusion layer. The cathode gas diffusion layer may again include a cathode micropore layer and a cathode electrode substrate.

FIG. 3 is a diagram schematically showing a principle of electricity generation of a fuel cell, and in the fuel cell, a most basic unit generating electricity is a membrane-electrode assembly (MEA), and this is formed with an electrolyte membrane (100), and anode (200a) and cathode (200b) electrodes formed on both sides of the electrolyte membrane (100). When referring to FIG. 1 showing a principle of electricity generation of a fuel cell, an oxidation reaction of fuel such as hydrogen, methanol, or hydrocarbon such as butane occurs in the anode (200a) to generate hydrogen ions (H$^+$) and electrons (e$^-$), and the hydrogen ions migrate to the cathode (200b) through the electrolyte membrane (100). In the cathode (200b), water is produced through the reaction of the hydrogen ions transferred through the electrolyte membrane (100), an oxidizer such as oxygen, and electrons. Electrons migrate to an external circuit through such a reaction.

The anode electrode catalyst layer is a place where an oxidation reaction of fuel occurs, and catalysts selected from the group consisting of platinum, ruthenium, osmium, platinum-ruthenium alloys, platinum-osmium alloys, platinum-palladium alloys and platinum-transition metal alloys may be preferably used. The cathode electrode catalyst layer is a place where a reduction reaction of an oxidizer occurs, and platinum or platinum-transition metal alloys may be preferably used as catalysts. The catalysts may be used as they are, or may be used while being supported on a carbon-based carrier.

The process of introducing the catalyst layer may be carried out using common methods known in the art, and for example, a catalyst ink may be directly coated on the electrolyte membrane, or coated on the gas diffusion layer to form the catalyst layer. Herein, the coating method of the catalyst ink is not particularly limited, and methods of spray coating, tape casting, screen printing, blade coating, die coating, spin coating or the like may be used. The catalyst ink may be typically formed with a catalyst, a polymer ionomer and a solvent.

The gas diffusion layer becomes a migration path of reaction gases and water while performing a role of a current conductor, and has a porous structure. Accordingly, the gas diffusion layer may be formed including a conductive substrate. As the conductive substrate, carbon paper, carbon cloth or carbon felt may be preferably used. The gas diffusion layer may be formed further including a micropore layer between the catalyst layer and the conductive substrate. The micropore layer may be used for enhancing fuel cell performance under a low humidity condition, and performs a role of allowing the electrolyte membrane to be under a sufficiently wet condition by having the amount of water escaping outside the gas diffusion layer being small.

One embodiment of the present specification provides a polymer electrolyte-type fuel cell including two or more membrane-electrode assemblies; a stack including a bipolar plate provided between the membrane-electrode assemblies; a fuel supplying unit supplying fuel to the stack; and an oxidizer supplying unit supplying an oxidizer to the stack.

In the present specification, the membrane-electrode assembly includes either the polymer electrolyte membrane or the reinforced membrane described above.

A fuel cell is an energy conversion device directly converting chemical energy of fuel into electric energy. In other words, a fuel cell employs a power generation method utilizing a fuel gas and an oxidizer, and using electrons generated during the oxidation and reduction reactions thereof to produce power.

The fuel cell may be prepared through common methods known in the art using the membrane-electrode assembly (MEA) described above. For example, the fuel cell may be prepared by forming with the membrane-electrode assembly (MEA) prepared above and a bipolar plate.

The fuel cell of the present specification is formed including a stack, a fuel supplying unit and an oxidizer supplying unit.

FIG. 5 is a diagram schematically illustrating the fuel cell, and the fuel cell is formed including a stack (60), an oxidizer supplying unit (70) and a fuel supplying unit (80).

The stack (60) includes one, two or more of the membrane-electrode assemblies described above, and when two or more of the membrane-electrode assemblies are included, a separator provided therebetween is included. The separator prevents the membrane-electrode assemblies from being electrically connected, and performs a role of transferring fuel and oxidizer supplied from the outside to the membrane-electrode assemblies.

The oxidizer supplying unit (70) performs a role of supplying an oxidizer to the stack (60). As the oxidizer, oxygen is typically used, and oxygen or air may be injected with a pump (70) to be used.

The fuel supplying unit (80) performs a role supplying fuel to the stack (60), and may be formed with a fuel tank (81) storing fuel, and a pump (82) supplying the fuel stored in the fuel tank (81) to the stack (60). As the fuel, hydrogen or hydrocarbon fuel in a gas or liquid state may be used. Examples of the hydrocarbon fuel may include methanol, ethanol, propanol, butanol or natural gas.

The fuel cell may include a polymer electrolyte fuel cell, a direct liquid fuel cell, a direct methanol fuel cell, a direct formic acid fuel cell, a direct ethanol fuel cell, a direct dimethyl ether fuel cell or the like.

When using the electrolyte membrane according to one embodiment of the present specification as an ion-exchange membrane of the fuel cell, effects described above may be obtained.

In addition, one embodiment of the present specification provides a redox flow battery including a positive electrode cell including a positive electrode and a positive electrode liquid electrolyte; a negative electrode cell including a negative electrode and a negative electrode liquid electrolyte; and the polymer electrolyte membrane according to one embodiment of the present specification provided between the positive electrode cell and the negative electrode cell.

Another embodiment provides a redox flow battery including a positive electrode cell including a positive electrode and a positive electrode liquid electrolyte; a negative electrode cell including a negative electrode and a negative electrode liquid electrolyte; and the reinforced membrane according to one embodiment of the present specification provided between the positive electrode cell and the negative electrode cell.

A redox flow battery (oxidation-reduction flow battery) is a system charged and discharged by active materials included in a liquid electrolyte being oxidized and reduced, and is an electrochemical storage device directly storing chemical energy of the active materials as electric energy. A redox flow battery uses a principle of being charged and discharged from the exchange of electrons occurring when liquid electrolytes including active materials in different oxidation states meet with an ion-exchange membrane in between. A redox flow battery is generally formed with a tank holding a liquid electrolyte, a battery cell where charge and discharge occur, and a circulating pump for circulating the liquid electrolyte between the tank and the battery cell, and a unit cell of the battery cell includes an electrode, an electrolyte and an ion-exchange membrane.

When using the electrolyte membrane according to one embodiment of the present specification as an ion-exchange membrane of the redox flow battery, effects described above may be obtained.

The redox flow battery of the present specification may be prepared using common methods known in the art except for including the polymer electrolyte membrane according to one embodiment of the present specification.

As illustrated in FIG. 4, the redox flow battery is divided into a positive electrode cell (32) and a negative electrode cell (33) by an electrolyte membrane (31). The positive electrode cell (32) and the negative electrode cell (33) include a positive electrode and a negative electrode, respectively. The positive electrode cell (32) is connected to a positive electrode tank (10) for supplying and releasing a positive electrode liquid electrolyte (41) through a pipe. The negative electrode cell (33) is also connected to a negative electrode tank (20) for supplying and releasing a negative electrode liquid electrolyte (42) through a pipe. The liquid electrolytes circulate through pumps (11, 21), and through an oxidation/reduction reaction (that is, a redox reaction) changing the oxidation number of ions, charge and discharge occur in the positive electrode and the negative electrode.

Hereinafter, the present specification will be described in detail with reference to examples. However, the examples according to the present specification may be modified to various other forms, and the scope of the present specification is not to be construed as being limited to the examples described below. Examples of the present specification are provided in order to more completely describe the present specification to those having average knowledge in the art.

\<Preparation Example 1\> Preparation of Chemical Formula 1-1

(1) Preparation of Chemical Formula A-1 (Synthesis of ((2-bromo-1,1,2,2-tetrafluoroethyl)(2,4-difluorophenyl)sulfane)

[Formula A-1]

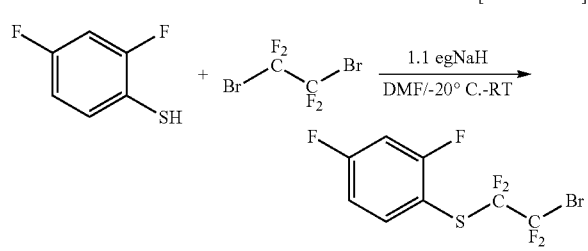

After dissolving 100.12 g (0.685 mol) of 2,4-difluorobenzenethiol in 1200 ml of dimethylformamide (DMF) and cooling the mixture to −20° C., 30.4 g (0.754 mol) of sodium hydride (NaH) was slowly added dropwise thereto in small aliquots, and the result was stirred for approximately 30 minutes at −20° C.

After 195.79 g (0.754 mol) of 1,2-dibromotetrafluoroethane was slowly added dropwise thereto at −20° C., the reaction temperature was slowly raised to room temperature. After reacting for approximately 2 hours, the reaction was terminated using a saturated aqueous ammonium chloride solution, and the reaction material was acidified with an aqueous 1 N hydrochloric acid solution, then extracted with ethyl acetate, and washed with salt water. The organic layer was separated, dried with magnesium sulfate (MgSO₄), distilled, and then separated and purified with column chromatography using hexane to obtain 163.25 g (73%) of the compound of Chemical Formula A-1.

FIG. 1 is a diagram showing an NMR graph of Chemical Formula A-1.

(2) Preparation of Chemical Formula A-2 (Synthesis of sodium-2-((2,4-difluorophenyl)thio)-1,1,2,2-tetrafluoroethane-1-sulfinate)

[Formula A-2]

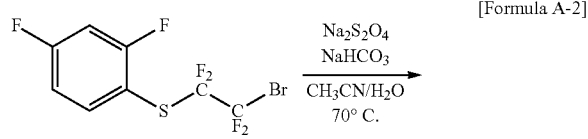

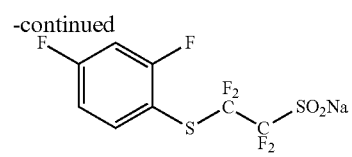

After dissolving 106.52 g (0.328 mol) of the compound of Chemical Formula A-1 obtained in Preparation Example (1) in MeCN/H₂O=800 ml/1170 ml, 201.4 g (0.983 mol) of sodium hydrosulfite (Na₂S₂O₄) and 82.60 g (0.983 mol) of sodium bicarbonate (NaHCO₃) were each added consecutively. After the reaction material was reacted for 2 hours to 3 hours at 70° C., the temperature was cooled to room temperature, and the result was vacuum distilled to remove the solvent. This compound was dried to obtain the compound of Chemical Formula A-2, a final compound.

(3) Preparation of Chemical Formula 1-1 (Synthesis of sodium-2-((2,4-difluorophenyl)thio)-1,1,2,2-tetrafluoroethane-1-sulfonic Acid)

[Formula 1-1]

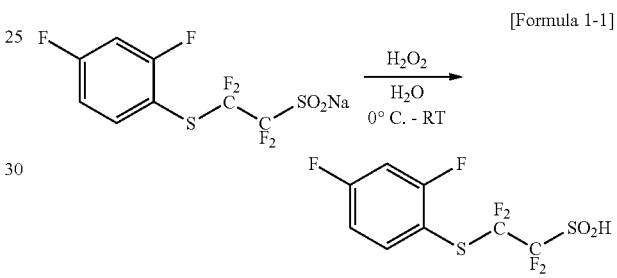

After dissolving 55.21 g (0.17 mol) of the compound of Chemical Formula A-2 obtained in Preparation Example (2) in 900 ml of water, the mixture was cooled to 0° C. 565.2 g (16.62 mol) of hydrogen peroxide was slowly added dropwise thereto, the result was reacted for 9 hours, and the solution was acidified by adding excess 1 N hydrochloric acid (HCl). The result was extracted with ethyl acetate, dried with magnesium sulfate (MgSO₄ and then the solvent was removed by distillation. This compound was dried to obtain 41.94 g (77.4%) of the compound of Chemical Formula 1-1.

FIG. 2 is a diagram showing an NMR graph of Chemical Formula 1-1.

\<Preparation Example 2\> Synthesis of Polymer

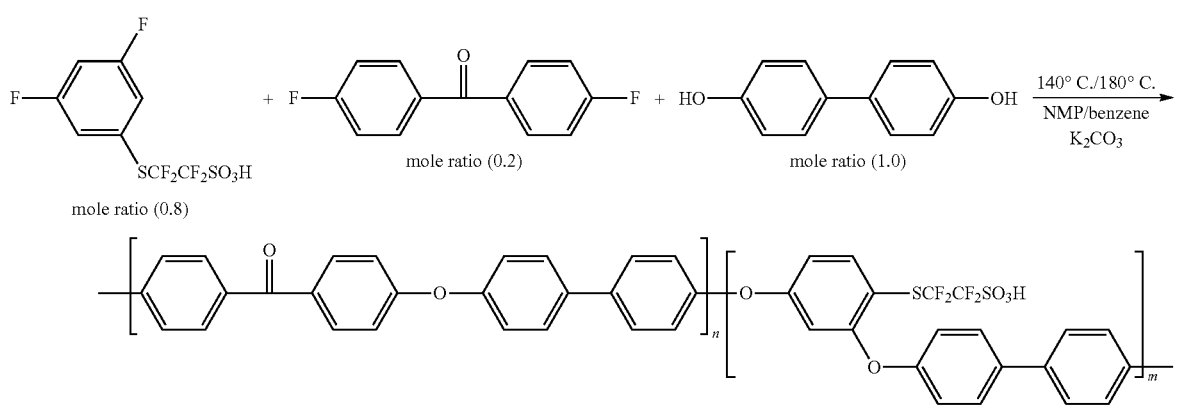

Each monomer and potassium carbonate ($K_2CO_3$: molar ratio 4) were mixed in ratios of 20 wt % NMP and 20 wt % benzene, and the result was polymerized for 4 hours at 140° C. and 16 hours at 180° C. to prepare the polymer.

In the following example and comparative examples, a separator was prepared using the polymer obtained in Preparation Example 2, the molecular weight was measured through GPC, and results of measuring cation conductivity and ion exchange capacity (IEC) of the pure membrane were described.

Example 1

A polymer was prepared using the method of Preparation Example 2, and a partial fluorine-based membrane was prepared and the molecular weight was measured through GPC, and cation conductivity and an ion exchange capacity (IEC) value were measured and are shown in Table 1.

TABLE 1

| Partial Fluorine-based Membrane | Mn (g/mol) | Mw (g/mol) | Mw/Mn | Ion Conductivity (S/cm) | IEC |
|---|---|---|---|---|---|
| Example 1 | 84,000 | 622,000 | 7.40 | 0.12 | 1.31 |

From the results of Table 1, it was identified that a polymer including a monomer derived from the halogenated compound according to one embodiment of the present specification had high ion conductivity and ion exchange capacity.

Comparative Example 1

A high molecular weight polymer was successfully obtained as a result of carrying out an experiment obtaining a polymer using a 2,4-difluoro partial fluorine-based monomer, the monomer of Chemical Formula 1-1 obtained in Preparation Example 1. However, obtaining a high molecular weight polymer was unsuccessful under the same condition when attempting to prepare a polymer using a generally used 2,5-difluoro partial fluorine-based monomer. The molecular weight of the polymer was measured through gel permeation chromatography (GPC) and the results are shown in the following Table 2.

Comparative Example 2

A polymer was attempted to be prepared in the same manner as in Comparative Example 1 using a $SO_2$ monomer instead of elemental S in Chemical Formula 2, however, obtaining a high molecular weight polymer was unsuccessful under the same condition. The molecular weight of the polymer was measured through gel permeation chromatography (GPC) and the results are shown in the following Table 2.

TABLE 2

| Partial Fluorine-based Membrane | Mn (g/mol) | Mw (g/mol) | Mw/Mn |
|---|---|---|---|
| Example 1 | 84,000 | 622,000 | 7.40 |
| Comparative Example 1 | N/A | N/A | N/A |
| Comparative Example 2 | N/A | N/A | N/A |

In Table 2, N/A means not available, and it was identified that the polymer was not formed.

Based on the results of Example 1 and Comparative Example 1, a monomer substituted with functional groups at 2 and 5 positions, which has been generally used in the art, has been commercially used without considering reactivity even when reactivity is very different during a polymerization reaction depending on the properties of functional group substituting other positions.

It can be identified that, by the functional group of Chemical Formula 2 hung as a pendant generally having an electron withdrawing characteristic, the 2,4-difluoro halogenated compound according to one embodiment of the present specification exhibits greatly enhanced reactivity during a polymerization reaction, which is advantageous in obtaining a high molecular weight polymer.

Based on the results of Example 1 and Comparative Example 2, it can be identified that a compound including at least one Chemical Formula 2 according to one embodiment of the present specification is chemically stable and readily form a polymer.

The invention claimed is:
1. A halogenated compound represented by the following Chemical Formula 1:

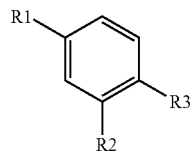

[Chemical Formula 1]

wherein, in Chemical Formula 1,
R1 to R3 are the same as or different from each other, and each independently represented by a halogen group; the following Chemical Formula 2; or the following Chemical Formula 3;
at least one of R1 to R3 is a halogen group;
at least one of R1 to R3 is the following Chemical Formula 2;

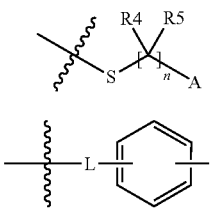

[Chemical Formula 2]

[Chemical Formula 3]

in Chemical Formulae 2 and 3,
A is $SO_3H$, $SO_3^-M^+$, —COOH, —COO$^-M^+$, —PO$_3H_2$, —PO$_3H^-M^+$, —PO$_3^{2-}2M^+$, —O(CF$_2$)$_m$SO$_3H$, —O(CF$_2$)$_m$SO$_3^-M^+$, —O(CF$_2$)$_m$COOH, —O(CF$_2$)$_m$COO$^-M^+$, —O(CF$_2$)$_m$PO$_3H_2$, —O(CF$_2$)$_m$PO$_3H^-$ $M^+$ or —O(CF$_2$)$_m$PO$_3^{2-}2M^+$;
m is an integer of 1 to 6;
M is a group 1 element;
R4 and R5 are the same as or different from each other, and each independently a halogen group;
n is an integer of 2 to 10, and structures in the 2 to 10 parentheses are the same as or different from each other;
L is O, S, $SO_2$, CO or $CF_2$; and
R6 is a hydroxyl group; or a halogen group.

2. The halogenated compound of claim 1, wherein R1 and R2 are a halogen group, and R3 is Chemical Formula 2.

3. The halogenated compound of claim 1, wherein the compound represented by Chemical Formula 1 is represented by any one of the following Chemical Formulae 1-1 to 1-9:

[Chemical Formula 1-1]
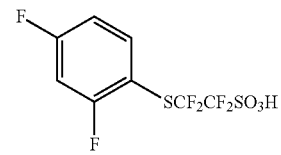

[Chemical Formula 1-2]
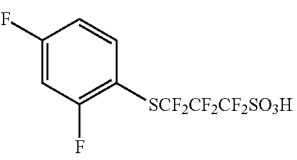

[Chemical Formula 1-3]
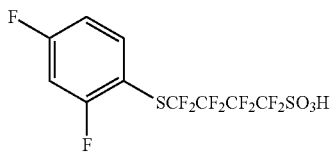

[Chemical Formula 1-4]
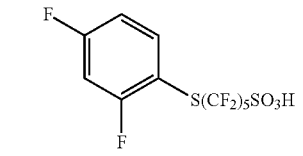

[Chemical Formula 1-5]
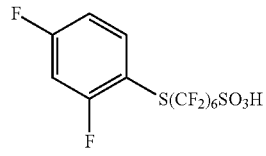

[Chemical Formula 1-6]
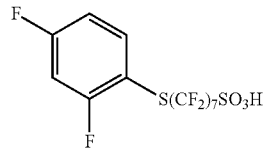

[Chemical Formula 1-7]
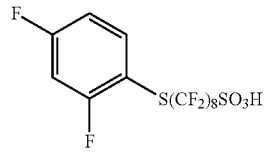

[Chemical Formula 1-8]
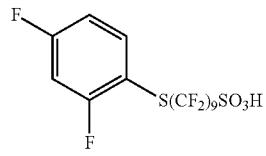

[Chemical Formula 1-9]
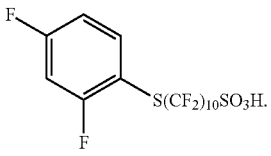

4. The halogenated compound of claim 1, wherein the structure represented by Chemical Formula 3 is represented by the following Chemical Formula 3-1 or Chemical Formula 3-2:

[Chemical Formula 3-1]
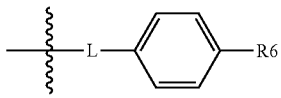

[Chemical Formula 3-2]
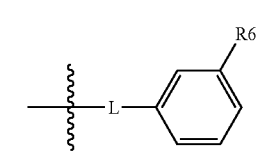

wherein, Chemical Formula 3-1 and Chemical Formula 3-2,
definitions of L and R6 are the same as in Chemical Formula 3.

5. The halogenated compound of claim 4, wherein R1 is Chemical Formula 3-1, R2 is Chemical Formula 2, and L is CO; $CF_2$; or $SO_2$.

6. The halogenated compound of claim 4, wherein R1 is Chemical Formula 3-2, R3 is Chemical Formula 2, and L is S; or O.

7. The halogenated compound of claim 1, wherein the compound represented by Chemical Formula 1 is represented by any one of the following Chemical Formulae 1-10 to 1-15:

[Chemical Formula 1-10]

[Chemical Formula 1-11]
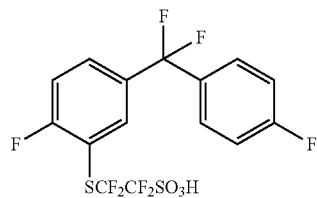

[Chemical Formula 1-12]
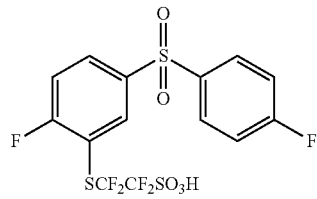

[Chemical Formula 1-13]
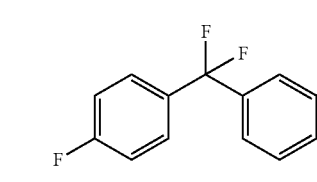

-continued

[Chemical Formula 1-14]

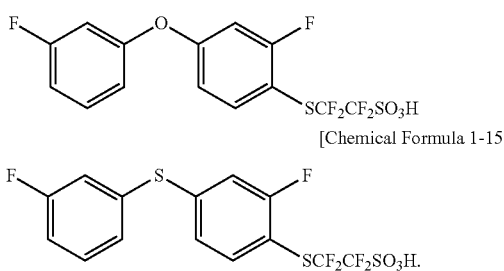

[Chemical Formula 1-15]

8. A polymer comprising a monomer derived from the halogenated compound of claim 1.

9. The polymer of claim 8 comprising the monomer derived from the halogenated compound in 1 mol % to 100 mol %.

10. The polymer of claim 8, which is a block polymer including a hydrophilic block; and a hydrophobic block, wherein the hydrophilic block includes the monomer derived from the halogenated compound.

11. The polymer of claim 10, wherein the hydrophilic block and the hydrophobic block are included in a ratio of 1:0.1 to 1:10 in the block polymer.

12. The polymer of claim 8, which has a weight average molecular weight of 500 g/mol to 5,000,000 g/mol.

13. A polymer electrolyte membrane comprising the polymer of claim 8.

14. A reinforced membrane comprising:
a substrate; and
the polymer of claim 8.

15. A membrane-electrode assembly comprising:
an anode;
a cathode; and
the polymer electrolyte membrane of claim 13 provided between the anode and the cathode.

16. A polymer electrolyte-type fuel cell comprising:
two or more of the membrane-electrode assemblies of claim 15;
a stack including a bipolar plate provided between the membrane-electrode assemblies;
a fuel supplying unit supplying fuel to the stack; and
an oxidizer supplying unit supplying an oxidizer to the stack.

17. A redox flow battery comprising:
a positive electrode cell including a positive electrode and a positive electrode liquid electrolyte;
a negative electrode cell including a negative electrode and a negative electrode liquid electrolyte; and
the polymer electrolyte membrane of claim 13 provided between the positive electrode cell and the negative electrode cell.

18. A membrane-electrode assembly comprising:
an anode;
a cathode; and
the reinforced membrane of claim 14 provided between the anode and the cathode.

19. A polymer electrolyte-type fuel cell comprising:
two or more of the membrane-electrode assemblies of claim 18;
a stack including a bipolar plate provided between the membrane-electrode assemblies;
a fuel supplying unit supplying fuel to the stack; and
an oxidizer supplying unit supplying an oxidizer to the stack.

20. A redox flow battery comprising:
a positive electrode cell including a positive electrode and a positive electrode liquid electrolyte;
a negative electrode cell including a negative electrode and a negative electrode liquid electrolyte; and
the reinforced membrane of claim 14 provided between the positive electrode cell and the negative electrode cell.

* * * * *